(12) United States Patent
Yomtov et al.

(10) Patent No.: US 7,917,208 B2
(45) Date of Patent: *Mar. 29, 2011

(54) MEDICAL DEVICE FOR CONTROLLED DRUG DELIVERY AND CARDIAC MONITORING AND/OR STIMULATION

(75) Inventors: Barry M. Yomtov, Marblehead, MA (US); Stephen J. Herman, Andover, MA (US)

(73) Assignee: MicroCHIPS, Inc., Bedford, MA (US)

( * ) Notice: Subject to any disclaimer, the term of this patent is extended or adjusted under 35 U.S.C. 154(b) by 85 days.

This patent is subject to a terminal disclaimer.

(21) Appl. No.: 10/679,772

(22) Filed: Oct. 6, 2003

(65) Prior Publication Data

US 2004/0106953 A1    Jun. 3, 2004

Related U.S. Application Data

(60) Provisional application No. 60/460,163, filed on Apr. 3, 2003, provisional application No. 60/444,554, filed on Feb. 3, 2003, provisional application No. 60/416,005, filed on Oct. 4, 2002.

(51) Int. Cl.
*A61N 1/362* (2006.01)
(52) U.S. Cl. ............................................ 607/3; 607/120
(58) Field of Classification Search ............... 607/3, 120
See application file for complete search history.

(56) References Cited

U.S. PATENT DOCUMENTS

| 4,003,379 | A | 1/1977 | Ellinwood, Jr. |
| 4,146,029 | A | 3/1979 | Ellinwood, Jr. |
| 4,360,019 | A | 11/1982 | Portner et al. |
| 4,360,031 | A | 11/1982 | White |
| 4,731,051 | A | 3/1988 | Fischell |
| 4,793,825 | A | 12/1988 | Benjamin et al. |
| 4,922,926 | A | 5/1990 | Hirschberg et al. |
| 5,041,107 | A | 8/1991 | Heil, Jr. |
| 5,067,491 | A | 11/1991 | Taylor, II et al. |

(Continued)

FOREIGN PATENT DOCUMENTS

DE    197 16 683 C1    6/1998

(Continued)

OTHER PUBLICATIONS

Bae, et al., "Pulsatile Drug Release by Electric Stimulus," ACS Symp. Series *Polymeric Drugs & Drug Admin.*, pp. 99-110 (1994).

(Continued)

*Primary Examiner* — Niketa I Patel
*Assistant Examiner* — Alyssa M Alter
(74) *Attorney, Agent, or Firm* — Sutherland Asbill & Brennan LLP

(57) ABSTRACT

Medical device and methods are provided for controlled drug delivery in a cardiac patient. The device includes an implantable drug delivery module comprising reservoirs containing a drug and a control means for selectively releasing an effective amount of drug from each reservoir; one or more electrodes or sensors for cardiac monitoring, stimulation, or both; and a microcontroller for controlling operational interaction of the drug delivery module and the cardiac electrode. The electrodes may comprise ECG monitoring, cardioversion, or cardiac pacing electrodes. A medical device also is provided for controlled delivery of drug to a patient having congestive heart failure, which includes an implantable drug delivery module comprising a natriuretic peptide and a release mechanism for selectively releasing a pharmaceutically effective amount of the natriuretic peptide into the patient; and a microcontroller for controlling the release mechanism, for example, in response to one or more monitored patient parameters.

39 Claims, 4 Drawing Sheets

U.S. PATENT DOCUMENTS

| | | | |
|---|---|---|---|
| 5,147,297 A | 9/1992 | Myers et al. | |
| 5,156,148 A | 10/1992 | Cohen | |
| 5,167,625 A | 12/1992 | Jacobsen et al. | |
| 5,200,051 A | 4/1993 | Cozzette et al. | |
| 5,252,294 A | 10/1993 | Kroy et al. | |
| 5,324,316 A | 6/1994 | Schulman et al. | |
| 5,366,454 A | 11/1994 | Currie et al. | |
| 5,368,588 A | 11/1994 | Bettinger | |
| 5,368,704 A | 11/1994 | Madou et al. | |
| 5,387,419 A | 2/1995 | Levy et al. | |
| 5,524,338 A | 6/1996 | Martyniuk et al. | |
| 5,556,421 A | 9/1996 | Prutchi et al. | |
| 5,562,715 A | 10/1996 | Czura et al. | |
| 5,662,689 A | 9/1997 | Elsberry et al. | |
| 5,713,954 A | 2/1998 | Rosenberg et al. | |
| 5,797,898 A | 8/1998 | Santini, Jr. et al. | |
| 5,807,397 A | 9/1998 | Barreras | |
| 5,971,931 A | 10/1999 | Raff | |
| 5,989,445 A | 11/1999 | Wise et al. | |
| 6,001,090 A | 12/1999 | Lenhart | |
| 6,051,017 A | 4/2000 | Loeb et al. | |
| 6,112,116 A * | 8/2000 | Fischell et al. | 600/517 |
| 6,114,658 A | 9/2000 | Roth et al. | |
| 6,123,861 A | 9/2000 | Santini, Jr. et al. | |
| 6,129,685 A | 10/2000 | Howard, III | |
| 6,161,047 A | 12/2000 | King et al. | |
| 6,178,349 B1 | 1/2001 | Kieval | |
| 6,185,455 B1 | 2/2001 | Loeb et al. | |
| 6,214,032 B1 | 4/2001 | Loeb et al. | |
| 6,243,608 B1 | 6/2001 | Pauly et al. | |
| 6,289,237 B1 | 9/2001 | Mickle et al. | |
| 6,319,241 B1 | 11/2001 | King et al. | |
| 6,328,699 B1 | 12/2001 | Eigler et al. | |
| 6,334,859 B1 | 1/2002 | Richter | |
| 6,349,232 B1 * | 2/2002 | Gordon | 604/20 |
| 6,453,195 B1 * | 9/2002 | Thompson | 607/3 |
| 6,491,666 B1 | 12/2002 | Santini, Jr. et al. | |
| 6,501,983 B1 | 12/2002 | Natarajan et al. | |
| 6,527,762 B1 * | 3/2003 | Santini et al. | 604/890.1 |
| 6,537,256 B2 | 3/2003 | Santini, Jr. et al. | |
| 6,551,838 B2 | 4/2003 | Santini, Jr. et al. | |
| 6,571,125 B2 | 5/2003 | Thompson | |
| 6,587,719 B1 | 7/2003 | Barrett et al. | |
| 6,656,162 B2 | 12/2003 | Santini, Jr. et al. | |
| 6,666,821 B2 | 12/2003 | Keimel | |
| 6,669,683 B2 | 12/2003 | Santini, Jr. et al. | |
| 6,726,920 B1 * | 4/2004 | Theeuwes et al. | 424/423 |
| 6,730,026 B2 | 5/2004 | Christ et al. | |
| 6,730,072 B2 | 5/2004 | Shawgo et al. | |
| 6,733,485 B1 | 5/2004 | Whitehurst et al. | |
| 6,757,560 B1 | 6/2004 | Fischer et al. | |
| 6,908,770 B1 | 6/2005 | McDevitt et al. | |
| 6,968,743 B2 | 11/2005 | Rich et al. | |
| 6,969,369 B2 | 11/2005 | Struble | |
| 7,010,345 B2 | 3/2006 | Hill et al. | |
| 2001/0053885 A1 | 12/2001 | Gielen et al. | |
| 2002/0038137 A1 | 3/2002 | Stein | |
| 2002/0055761 A1 | 5/2002 | Mann et al. | |
| 2002/0072784 A1 * | 6/2002 | Sheppard et al. | 607/60 |
| 2002/0082665 A1 | 6/2002 | Haller et al. | |
| 2002/0082680 A1 | 6/2002 | Shanley et al. | |
| 2002/0099359 A1 | 7/2002 | Santini, Jr. et al. | |
| 2002/0107470 A1 | 8/2002 | Richards et al. | |
| 2002/0107553 A1 | 8/2002 | Hill et al. | |
| 2002/0111601 A1 | 8/2002 | Thompson | |
| 2002/0111658 A1 | 8/2002 | Greenberg et al. | |
| 2002/0138067 A1 | 9/2002 | Sheppard, Jr. et al. | |
| 2002/0143369 A1 | 10/2002 | Hill et al. | |
| 2002/0151776 A1 | 10/2002 | Shawgo et al. | |
| 2002/0165586 A1 | 11/2002 | Hill et al. | |
| 2002/0183721 A1 | 12/2002 | Santini, Jr. et al. | |
| 2002/0187260 A1 | 12/2002 | Sheppard, Jr. et al. | |
| 2002/0188282 A1 | 12/2002 | Greenberg | |
| 2003/0004549 A1 | 1/2003 | Hill et al. | |
| 2003/0010808 A1 | 1/2003 | Uhland et al. | |
| 2003/0036794 A1 | 2/2003 | Ragheb et al. | |
| 2003/0055344 A1 | 3/2003 | Eigler et al. | |
| 2003/0055345 A1 | 3/2003 | Eigler et al. | |
| 2003/0104590 A1 | 6/2003 | Santini, Jr. et al. | |
| 2003/0105455 A1 | 6/2003 | Santini, Jr. et al. | |
| 2004/0082937 A1 * | 4/2004 | Ausiello et al. | 604/891.1 |
| 2004/0106914 A1 | 6/2004 | Coppeta et al. | |
| 2004/0121486 A1 | 6/2004 | Uhland et al. | |
| 2004/0127942 A1 * | 7/2004 | Yomtov et al. | 607/3 |
| 2005/0049472 A1 | 3/2005 | Manda et al. | |
| 2005/0100937 A1 | 5/2005 | Holmes | |
| 2006/0041296 A1 | 2/2006 | Bauer et al. | |
| 2006/0074404 A1 | 4/2006 | Struble | |

FOREIGN PATENT DOCUMENTS

| | | |
|---|---|---|
| WO | WO 94/21237 | 9/1994 |
| WO | WO 01/28629 A1 | 4/2001 |
| WO | WO 01/37926 A1 | 5/2001 |
| WO | WO 02/056862 A2 | 7/2002 |

OTHER PUBLICATIONS

Haroun, et al., "Local Drug Delivery," *Curr Opin. Oncol.* 12(3): 187-93 (2000) (abstract).

Liu, et al., "Applications of Microfabrication and Micromachining Techniques to Biotechnology," *Tibtech* 15: 213-16 (1997).

Santini, et al., "Microchips as Controlled Drug-Delivery Devices" *Angew Chem. Int. Ed. Engl.* 39(14): 2396-407 (2000).

Santini, et al., "Microchip Technology in Drug Delivery," *Ann. Med.* 32(6) 377-79 (2001).

Santini, et al., "A Controlled-Release Microchip," *Nature* 397(6717): 335-38 (1999).

Tao, et al., "Microfabricated Drug Delivery Systems: From Particles to Pores," *Adv. Drug Deliv. Res.* 55(3): 315-28 (2003).

Izrailtyan, et al. "*Early Detection of Acute Allograft Rejection by Linear and Nonlinear Analysis of Heart Rate Variability*", Cardiothoracic Transplantation, 120(4): 737-45 (Oct. 2000).

Colucci, et al. "*Intravenous Nesiritide, A Natriuretic Peptide, in the Treatment of Decompensated Congestive Heart Failure*", 343:246-253 (Jul. 2000).

* cited by examiner

Implantable Drug Delivery Module
With Implantable ECG Monitoring

MEDICAL DEVICE FOR CONTROLLED DRUG DELIVERY AND CARDIAC MONITORING AND/OR STIMULATION

CROSS-REFERENCE TO RELATED APPLICATIONS

Priority is claimed to U.S. Provisional Application No. 60/416,005, filed Oct. 4, 2002; to U.S. Provisional Application No. 60/444,554, filed Feb. 3, 2003; and to U.S. Provisional Application No. 60/460,163, filed Apr. 3, 2003. These applications are incorporated herein by reference.

BACKGROUND OF THE INVENTION

This invention is generally in the field of methods and devices for the delivery of drugs, the delivery or measurement of electrical signals, or a combination thereof, in the treatment and control of cardiac diseases or disorders.

The application of electrical energy to myocardial tissue has been an important mode of therapy to treat several cardiac conditions. For example, in the presence of bradycardia, implanted cardiac pacemakers are routinely used to sense slow heart rates and deliver properly timed pulses of electricity of specified pulse amplitude and pulse duration to control the sequence (in the case of dual chambered pacemakers) and the rate of the heart beat. Another example is in the response to unexpected ventricular tachy-arrhythmias such as ventricular tachycardia and ventricular fibrillation, for which the implantation of cardioverters is indicated. These devices deliver a pulse of electrical energy to cardiovert, or defibrillate, the heart (i.e., to cause the heart to revert to normal beating) when a clinically significant ventricular arrhythmia is detected. Implanted defibrillators have also been used to treat patients with atrial fibrillation.

In addition, monitoring of the electrical activity of the heart has been done for many applications. For example, the 12-lead surface ECG looks at the resting state of the heart, as well as the ECG response to stress conditions. These methods may be used for indications of coronary heart disease. Ambulatory monitoring of the surface ECG has been used for monitoring patients for abnormal arrhythmias, as well as for monitoring the ST segment for occurrences of silent ischemia as a possible predictor for myocardial infarction (MI). Other applications have also included monitoring patients with transplanted hearts for transplant rejection. One feature of external ECG monitoring devices is the inclusion of heart rate variability monitoring as a predictive variable for sudden cardiac death or heart transplantation rejection. Within the field of implantable devices, heart monitoring for abnormal arrhythmias, episodes of syncopy, and heart failure have been documented. Implantable pacemakers and defibrillators also have increased their monitoring capabilities.

U.S. Patent Application No. 2002/0107553 A1 discloses an apparatus for treating ventricular dysfunction, heart failure, or imbalance of autonomic tone or endocrinological system, comprising at least one electrode located in a region associated with cardiac tissue in a patient's body; and means for applying electrical stimulation via the at least one electrode to improve the cardiac efficiency of the patient's heart. The apparatus can further include a drug delivery pump coupled to a drug delivery catheter that may be used with cardiac stimulation to provide a biologically-active agent to tissue to prevent anticipated or detected physiological insults. It would be desirable to provide improved and/or alternative therapeutic devices and methods useful in treating or managing cardiac diseases and disorders, including arrhythmias. It would be desirable to provide implantable devices providing enhanced control of drug delivery in an apparatus for the delivery or monitoring of electrical signals to and from tissues in cardiac applications.

Congestive heart failure (CHF) is a chronic condition in which the heart does not pump sufficient blood to meet the body's needs. Typical symptoms are relatively non-specific, but include shortness of breath (dyspnea), fatigue, peripheral limb swelling (edema), fluid in the lungs (pulmonary congestion), weight gain, and abnormal lung sounds (rales). The underlying causes of these symptoms are fluid overload, vasoconstriction, and reduced myocardial contractility. Frequently, the patient's dyspnea becomes more severe than usual, resulting in admission to an emergency room for relief. Traditional intervention has involved the administration of diuretics, vasodilators, and drugs that improve contractility (inotropic agents). Such therapy is palliative; 50% of admitted patients are readmitted with similar symptoms within six months. In 2001, an estimated 1M patients were admitted to U.S. hospitals for CHF; it is the single largest expense for Medicare, at greater than $38B annually.

Within the past 15 years, three specific hormones have been identified which are expressed in response to CHF. Atrial natriuretic peptide (ANP) is expressed by cells in the cardiac atria during atrial distension. B-type (or brain) natriuretic peptide (BNP) is expressed by cells in the ventricular myocardium during overload or stretch. C-type natriuretic peptide (CNP) is released by cells in the endothelium in response to shear stress. When these hormones are released, they produce vasodilation, excretion of sodium, reduction in aldosterone levels, inhibition of the renin-angiotension aldosterone system, and inhibition of sympathetic nervous activity. All of these effects are beneficial to the CHF patient. It has also been reported that natriuretic peptides can modulate the remodeling of the heart muscle, which is a typical occurrence in CHF patients in response to the increased pumping demand (Naohisa, et al., "Cardiac fibrosis in mice lacking brain natriuretic peptide," *PNAS* 97(8):4239-44 (2000)). In addition, a rapid, bedside assay for BNP is available to facilitate diagnosis of CHF and its severity, and has been demonstrated to predict future CHF-related cardiac events. Unfortunately, in patients with severe CHF, the positive effects of these hormones, in the quantities that they are naturally expressed, are insufficient to relieve the symptoms. As a palliative strategy, a recombinant form of human BNP has been developed (Natracor-Scios, Inc.) and is becoming a common in-hospital intervention for progressive CHF, including acute episodes of severe dyspnea. Typical in-hospital intravenous (IV) administration includes a loading bolus of 2 μg/kg (~140 μg), followed by infusion of 0.01 μg/kg/min for 24 hrs (~1000 μg) or for 48 hours (~2000 μg). Blood pressure is routinely monitored due to the potential for hypotension.

It is desirable to intervene in CHF as early as possible, in order to preempt, or at least delay onset of, acute episodes of dyspnea. In many cases, administration of one or more drugs is a central part of the intervention. However, the administration of drugs in such circumstances may be problematic, in that the one or more drugs need to be administered over an extended period of time, to maintain the desired bioavailability of drug over time. A key limitation is patient compliance, particularly in the absence of acute symptoms, in that patients are often unwilling to accept (painful) daily or even weekly injections as the drug delivery means for extended periods. Moreover, for those drugs that can be (non-painfully) administered orally, the patients may forget to take them on schedule or at all. To deal with these strategies and limitations, a number of pharmaceutical companies have developed extended release formulations for numerous drugs, whether for oral or parenteral administration. These formulations typically rely, for example, on PEGylation or controlled release formulations, in an effort to avoid RES (reticuloendothelial system) uptake and control plasma drug levels for the purpose of extending the period between injections. Overall, this strategy has had mixed results, in part, because for many of the approaches, the strategy or technique employed for one drug is not readily transferable to another drug. It would therefore be desirable to provide a drug delivery system which avoids the need for frequent or continuous parenteral administration for use in the management or treatment of a variety of diseases, disorders, or conditions. It would also be desirable to reduce or obviate the need for a patient suffering from CHF to be admitted to a hospital for treatment of acute symptoms, preferably by providing a means for earlier drug intervention, particular in combination with a means for monitoring the patient's cardiovascular and other properties. Such an early intervention system would be highly desirable in the management of CHF or in other therapeutic or prophylactic applications.

SUMMARY OF THE INVENTION

Medical device and methods are provided for controlled drug delivery in cardiac care of a patient. In one aspect, the device includes an implantable drug delivery module which comprises a plurality of reservoirs, a release system contained in each of the reservoirs, wherein the release system comprises at least one drug, and a control means for selectively releasing a pharmaceutically effective amount of the drug from each of the reservoirs; one or more electrodes or sensors for operable engagement with a cardiac tissue of a patient, wherein the one or more electrodes are useful for cardiac monitoring, cardiac stimulation, or both; and at least one microcontroller for controlling operational interaction of the drug delivery module and the cardiac electrode. The electrodes may comprise ECG monitoring electrodes, cardioversion electrodes, cardiac pacing electrodes, or a combination thereof. The device may further include a power source. In addition, the device may further include telemetry components for communications with the microcontroller, the drug delivery module, the electrodes, the patient, or a combination thereof. In one embodiment, the device further comprises one or more physiological sensors operable to deliver a signal to the microcontroller.

Various drugs can be released depending on the particular therapeutic application and patient needs. In one embodiment, the drug, upon release, is effective to reduce the amount of energy required to cardiovert the heart. In one embodiment, the drug, upon release, is effective to stabilize an arrhythmia.

In one embodiment, the microcontroller causes the drug to be released from the drug delivery module immediately upon receiving a signal from the one or more electrodes indicative of onset of an arrhythmia. In one embodiment, the device is useful in the treatment of ventricular arrythmias.

In one variation, the device is used for detecting non-sustained ventricular tachycardias, changes in heart rate variability, or both, and it optionally may further include a defibrillator for delivering a cardioversion shock. This embodiment may be useful in the treatment of atrial fibrillation, and the drug may include an anti-coagulant, an analgesic, or both. In one specific embodiment, the microcontroller, upon receiving a signal from the one or more electrodes indicative of an atrial fibrillation, releases the drug and then after a predetermined delay initiates the cardioversion shock, wherein the delay is of a duration effective to permit the drug to take effect. Following the predetermined delay, the device optionally reconfirms the arrhythmia and, if detected, delivers the cardioversion shock.

In another embodiment, the device further includes a pacemaker having electrodes for contacting the cardiac muscle for monitoring of a patient and transmission of pacing signals. In one variation, the drug includes an anti-arrhythmic drug, which, upon release, is effective to reduce the frequency of induced pacing activity. In another variation, the drug, upon release, is effective to increase the sensitivity of myocardial tissue to the pacemaker stimulation pulse to effectively reduce pacing thresholds.

In another embodiment, the device includes a cardioversion means which comprises a signal generator connected to at least two of the electrodes, wherein the microcontroller controls the signal generator and the control means of the drug delivery module. In one specific embodiment, the cardioversion means is implantable.

In one embodiment, the device includes an ECG monitor for monitoring for a change in heart rate variability. This could be used for example in a patient having a transplanted heart, wherein the drug, upon release, is used to reduce heart transplant rejection and the monitor measures heart rate variability on a daily basis, and if the variability increases, then a secondary drug or higher dose of drug is delivered to the patient. In another example, the drug, upon release, is effective to prevent angina or myocardial infarction or both. In one embodiment, release of the drug is a function of the changes in the ST segment measured by the ECG monitor.

In another embodiment, the device includes a cardiac monitoring mean for measuring electrogram signals from the heart, wherein the microcontroller receives a signal from the cardiac monitoring means and controls the control means of the drug delivery module. In one variation, the cardiac monitoring means is implantable.

In one embodiment of the device, the one or more electrodes or sensors are on an outer surface of a hermetically sealed encasement containing the drug delivery module and the microcontroller. In another embodiment, the one or more electrodes or sensors extend a distance from a hermetically sealed encasement containing the drug delivery module and microcontroller. For example, a flexible catheter can connect the one or more electrodes or sensors to the encasement.

In one embodiment, the drug delivery module comprises a microchip drug delivery device. In one embodiment, the control means for selectively releasing a pharmaceutically effective amount of the drug comprises a reservoir cap positioned over each reservoir and a means for actively disintegrating the reservoir cap. For example, the reservoir cap in one embodiment is electrically conductive and the means for actively disintegrating the reservoir cap comprises an input lead and an output lead each connected to the reservoir cap and a power source for delivering an effective amount of electrical current through the reservoir cap, via the input lead and output lead, to heat and rupture the reservoir cap to release the drug.

In another aspect, a method is provided for treating a patient in need of cardiotherapy. In one embodiment, the method includes the steps of (i) implanting into the patient the medical device described herein, so as to operably engage the one or more electrodes with cardiac tissue in the patient; monitor one or more conditions of the heart with the electrodes or delivering electric stimulation to the heart or both; and (ii) releasing one or more drugs from the drug delivery module. In one specific embodiment, the one or more drugs are released based on ECG signals from the patient's heart. For example, the ECG signal can be monitored for a change in heart rate variability which is indicative of an oncoming sudden cardiac death, and the one or more drugs are released, if and when needed, to prevent sudden cardiac death. In another example, the ECG signal can be monitored for a change in heart rate variability which is indicative of rejection of a transplanted heart in the patient, and the one or more drugs are released, if and when needed, to prevent transplant rejection.

In another aspect, a medical device is provided for the controlled delivery of drug to a patient suffering from congestive heart failure. In one embodiment, the device includes an implantable drug delivery module which comprises a drug formulation of a natriuretic peptide and a release mechanism for selectively releasing a pharmaceutically effective amount of the natriuretic peptide into the patient; and at least one microcontroller for controlling the release mechanism. The microcontroller may operate in response to one or more monitored patient parameters, such as blood pressure, cardiac electrical signals, tissue electrical impedance, blood oxygen, blood oxygen saturation, natriuretic peptide levels, body weight, and combinations thereof. In one embodiment, the device further includes an implantable monitoring module which monitors hemodynamic parameters, ECG parameters, or both, for use in determining the one or more patient parameters. Interaction of the drug delivery module and the monitoring module can be controlled by the at least one microcontroller. In one embodiment, the drug delivery module further comprises a second drug, such as diuretics, vasodilators, inotropic agents, anti-arrhythmic agents, $Ca^+$ channel blocking agents, anti-adrenergics, sympatholytics, renin angiotensin system antagonists, or combinations thereof; and a second release mechanism for selectively releasing a pharmaceutically effective amount of the second drug into the patient. In one embodiment, the microcontroller comprises telemetry components for receiving instructions for releasing the drug formulation, the instructions being based on the one or more monitored patient parameters. In one variation, the patient parameters comprise external measurements.

In another aspect, a method is provided for treating a patient suffering from congestive heart failure. In one embodiment, the method includes the steps of (i) implanting a drug delivery module in a patient which can selectively release one or more drugs into the patient which are useful in the management or treatment of congestive heart failure; and (ii) releasing the one or more drugs from the implanted module, for example, in response to one or more monitored patient parameters. In a preferred embodiment, the one or more drugs include a natriuretic peptide. In variations of this method, the monitored patient parameters are selected from blood pressure, cardiac electrical signals, tissue electrical impedance, blood oxygen, blood oxygen saturation, natriuretic peptide levels, body weight, and combinations thereof. In one embodiment, the method further includes implanting a monitoring module in the patient and monitoring one or more patient parameters. Interaction of the drug delivery module and the monitoring module can be controlled by at least one microcontroller.

DESCRIPTION OF THE INVENTION

Figure 1:
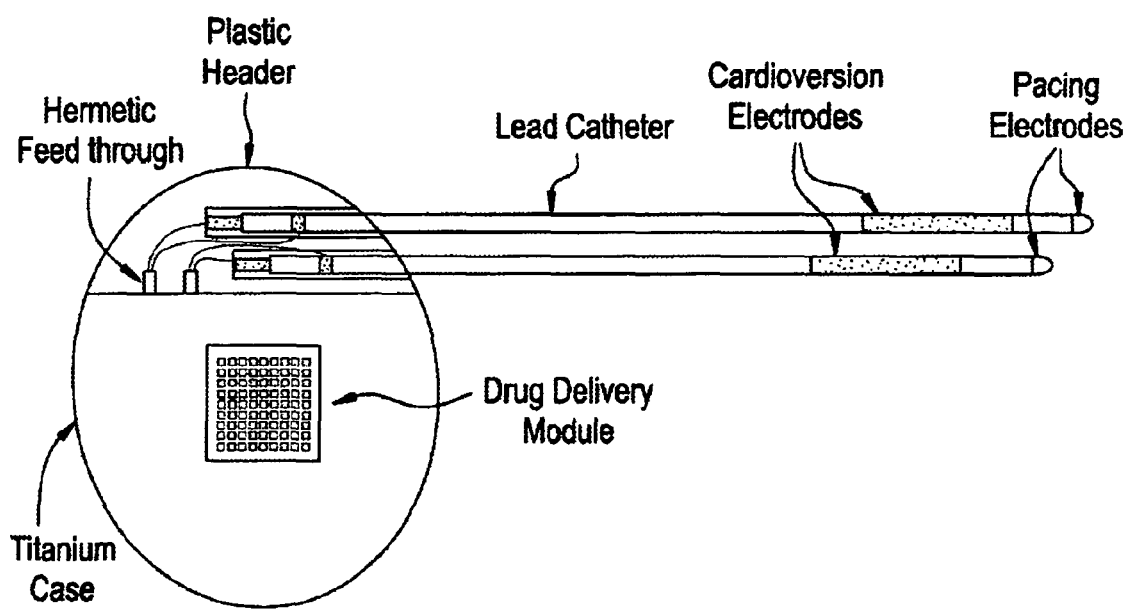
FIG. 1 is a plan view of one embodiment of the medical device described herein, comprising cardioversion electrodes, pacing electrodes, and a drug delivery module.

Medical devices are provided for use in the controlled delivery of drug for cardiac therapeutic applications, in combination with monitoring and/or stimulation of cardiac tissues. In one aspect, the medical devices are useful for treating patients suffering from diseases and disorders that may be better treated or managed with a combination of electrical stimulation and drug therapy. For example, the drug may augment the stimulation therapy, it may negate a side effect of the stimulation therapy, or it may reduce the stimulation threshold in the treatment. In another aspect, implantable drug delivery devices are provided for use in the management of congestive heart failure.

As used herein, the terms "comprise," "comprising," "include," and "including" are intended to be open, non-limiting terms, unless the contrary is expressly indicated.

In one embodiment, an implantable medical device is provided for use in arrhythmia therapy, which includes a drug delivery module and an arrhythmia control module.

In another embodiment, the implanted device comprises a cardioversion device and a drug delivery microchip that can release appropriate drugs in conjunction with the cardioversion therapy. In one embodiment, the microchip delivers a drug effective to reduce the amount of energy required to cardiovert the heart. In another embodiment, the microchip device delivers a drug that is effective to stabilize arrhythmias. Examples of such a drug include amiodarone, quinidine, and procainide. In a preferred embodiment, the drug is administered at the earliest detected onset of arrhythmias (e.g., detection of non-sustained ventricular tachycardias, or detection of changes in heart rate variability). The release-triggering signal to the drug delivery microchip could be provided by the cardioversion device. The drug delivery microchip could be integral within the cardioversion device and utilize its electronic and software capabilities.

One of the concerns of cardioversion in the treatment of atrial fibrillation is the potential release of blood clots that may have formed within the atria during the irregular beating. The release of clots after the atria are defibrillated, often result in an occlusive stroke. As atrial fibrillation is not an immediate life threatening arrhythmia, one embodiment of the implantable device provides that, at the onset of the detection of the atrial fibrillation, an anti-coagulant (such as coumadin, heparin, aspirin, etc.) is delivered to prevent clotting of the blood when the cardioversion shock is administered. When atrial fibrillation is detected, a predetermined time delay could be set to allow the drugs to take effect. Once this delay period has passed, the defibrillator could then reconfirm the arrhythmia and, if detected, the defibrillator would deliver the cardioversion therapy accordingly.

As atrial fibrillation is not considered life threatening, a patient's quality of life must be considered in the use of an implantable atrial defibrillator. The use of high levels of electrical energy for cardioversion may result in significant side effects to the patient. For example, the energy delivered by an implantable defibrillator (e.g., up to 10 joules for atrial defibrillation) can be startling and painful for the patient. Therefore, in one embodiment of the implantable device, an analgesic drug is delivered to reduce the discomfort usually associated with the delivery of the cardioversion shock. Examples of such drugs include Valium and lidocaine. These drugs can be introduced before the delivery of the cardioversion shock, thus providing improved quality of life when receiving this form of antiarrhythmic therapy.

Long term pacing patients often develop scar tissue around the electrodes that contact the cardiac muscle. This scar tissue can interfere with monitoring of the patient by the pacemaker and transmission of pacing signals. The typical response to this condition is to increase the amplitude of the pacing signal, which can induce pacing irregularity and diminish battery life. Therefore, in one embodiment of the implantable device used in cardiac pacing, the microchip device could be used to intermittently deliver an anti-arrhythmic drug to reduce the frequency of induced pacing activity. The benefit to be derived is that less scar tissue would be formed. In another embodiment, the microchip device delivers a drug effective to reduce the pacing threshold by increasing the sensitivity of the myocardial tissue to the pacemaker stimulation pulse. By reducing the pacing threshold, less energy is required to stimulate the heart thus increasing the longevity of the pacemaker.

The devices described herein are useful in several methods of arrhythmia therapy. Preferably, the devices provide doses of one or more drugs from an integral drug delivery microchip before the delivery of electrical cardioversion therapy. The delivery of antiarrhythmic drugs that can be administered at the early detection of the onset of an arrhythmia should reduce the risk of developing a more lethal arrhythmia. The devices can also be effective in (1) reducing pain perceived by the patient as the result of delivering a cardioversion shock, (2) lowering pacing thresholds, (3) reducing blood clotting prior to the delivery of a cardioversion shock to prevent potential strokes, (4) lowering cardioversion threshold, or (5) combinations thereof.

In another aspect of the invention, a device is provided for use in cardiac monitoring, which includes an implantable microchip device for drug delivery in response to changes in the monitored electrical cardiac signals. The devices described herein are useful in several methods of monitoring and responding to cardiac problems. For example, an implantable device could be useful in the prevention of myocardial infarction, lethal ventricular arrhythmias, and/or heart transplantation rejection. In one embodiment, the implantable device is used to help prevent heart transplant rejection. For example, the implantable device can be used to monitor the ECG of the heart and respond to changes in heart rate variability by administering one or more drugs effective to prevent heart transplant rejection. For example, an anti-rejection drug could be administered at a prescribed rate at regular intervals, while the heart rate variability is monitored on a daily basis. If the heart rate variability increases, which may be an indication of heart transplant rejection, then an alternate prescription can be administered. This alternate prescription could be a different dosage of the prescribed drug, a secondary drug contained in the microchip device, or both.

In another embodiment, the implantable device can be used to monitor the ECG of the heart and respond to changes in the ST segment by administering one or more drugs effective to prevent angina and/or myocardial infarction.

In yet another embodiment, the medical device is specifically adapted for the treatment or management of congestive heart failure. For example, in one device, the drug delivery module releases a natriuretic peptide.

I. Device Components and Materials

In one embodiment, the device for use in cardiotherapy comprises (i) an implantable drug delivery module which includes a plurality of reservoirs, a release system contained in each of the reservoirs, wherein the release system comprises at least one drug, and a control means for selectively releasing a pharmaceutically effective amount of the drug from each of the reservoirs; (ii) a cardioversion means which comprises a signal generator connected to at least two electrodes suitable for operable engagement with a cardiac muscle of a patient; and (iii) a microcontroller for controlling the signal generator and the control means of the drug delivery module. One embodiment of this device is illustrated in a plan view in FIG. 1.

Figure 3:
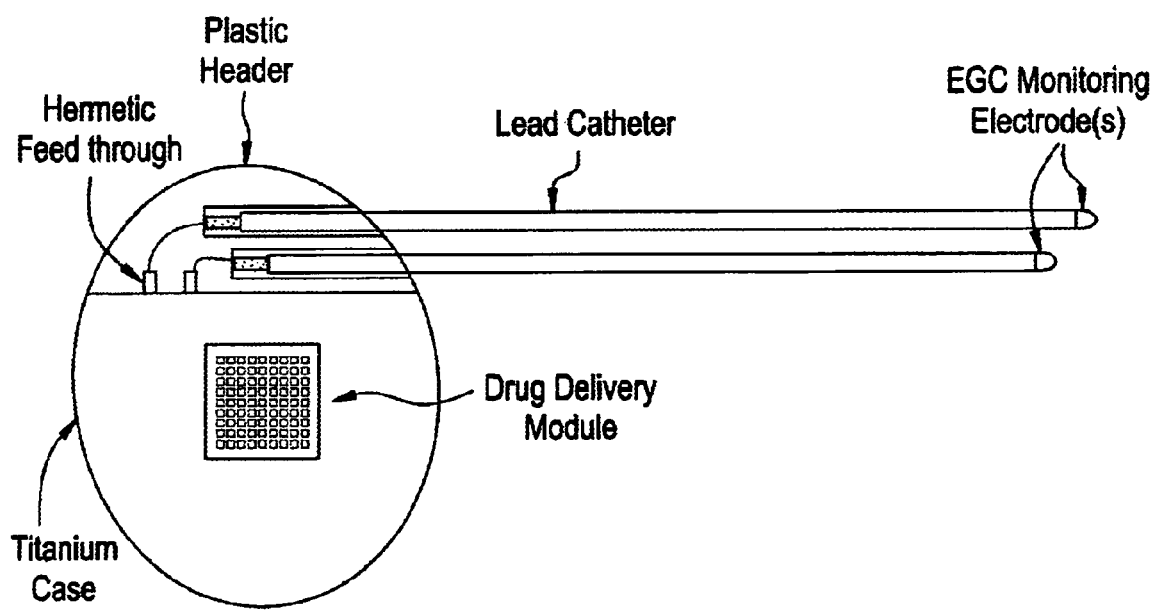
FIG. 3 is a plan view of one embodiment of the medical device described herein, comprising catheter-type ECG monitoring electrodes.
Figure 4:
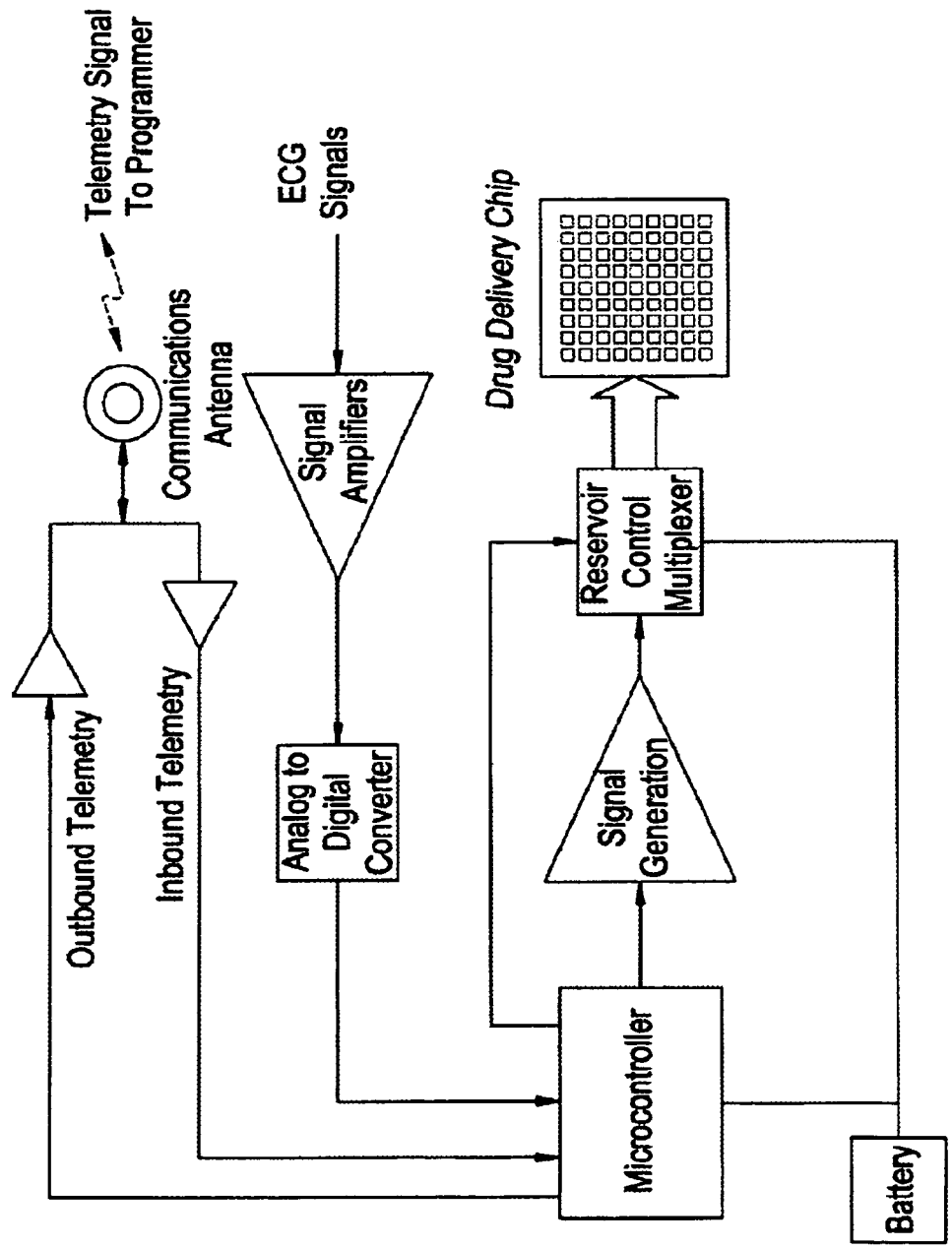
FIG. 4 is a schematic drawing of the components in one embodiment of the medical device described herein.

In another embodiment, the device for controlled drug delivery and heart monitoring comprises (i) an implantable drug delivery module which includes a plurality of reservoirs, a release system contained in each of the reservoirs, wherein the release system comprises at least one drug, and a control means for selectively releasing a pharmaceutically effective amount of the drug from each of the reservoirs; (ii) a cardiac monitoring means for measuring electrogram signals from the heart; and (iii) a microcontroller for receiving a signal from the cardiac monitoring means and for controlling the control means of the drug delivery module. Various embodiments of this device are illustrated in plan view in FIG. 2 and FIG. 3, and schematically in FIG. 4.

Figure 2:
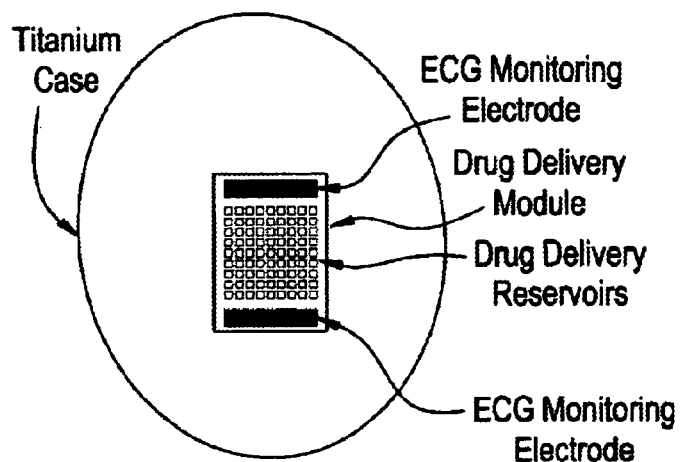
FIG. 2 is a plan view of one embodiment of the medical device described herein, comprising ECG monitoring electrodes on the same substrate as an array of drug-containing reservoirs positioned on a surface of a titanium encasement.

In one embodiment, the entire therapeutic device is implanted into the body of the patient at a single location, such that the electrodes are mounted onto a surface of the medical device (see, e.g., FIG. 2). In another embodiment, the drug delivery module of the device is implanted at a first location and the electrodes extend to cardiac tissue at another location, such as with a catheter. see, e.g., FIGS. 1 and 3.

Figure 5:
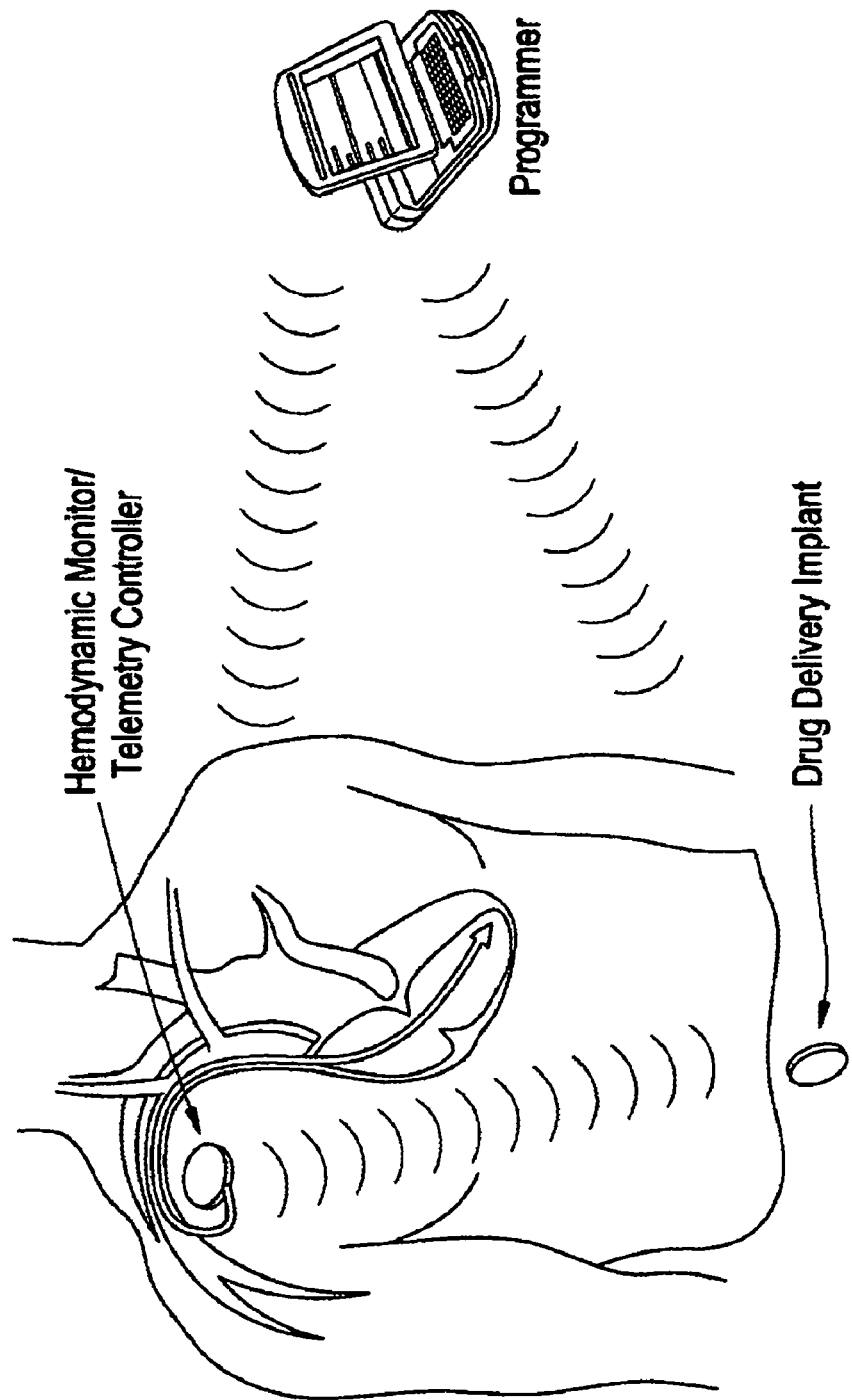
FIG. 5 is a diagram showing one embodiment of the medical device having a drug delivery module implanted at a first location in a patient, a hemodynamic monitor implanted at a second location in the patient, and a remote programmer device. The three components are in operable communication by telemetry.

In yet another embodiment, the drug delivery module of the device (e.g., a microchip device) is "free-standing" from the cardiac stimulator portion of entire device (i.e., the stimulator module—such as for pacing or defibrillation). The drug delivery module is implanted and controlled by a telemetry or hardwired signal from the stimulator module. See, e.g., FIG. 5. In this embodiment, there may be two microcontrollers: one for the stimulator module and one for the drug delivery module. The stimulator module could be implanted or used externally. One example of the latter would be the use of an external defibrillator or external pacing unit in combination with an implantable drug delivery system or module. (See, e.g., http://www.zoll.com, which describes such external devices.) When both modules are implanted, they can be replaced independently at the required intervals, e.g., the drug delivery module when the drugs have been expended and the stimulator when the battery is depleted.

B. The Controlled Drug Delivery Module

The drug delivery device includes a substrate having a plurality of reservoirs, which contain the drug molecules for delivery. In one embodiment, the drug delivery module comprises a microchip drug delivery device. The substrate, reservoirs, reservoir caps, control circuitry, and power source are described at least in part herein and/or in U.S. Pat. No. 5,797,898, No. 6,123,861, No. 6,551,838, No. 6,491,666, and No. 6,527,762, as well as U.S. Patent Application Publications No. 2002/0138067, No. 2002/0072784, No. 2002/0151776, and No. 2002/0107470.

In one embodiment, control of reservoir cap opening includes electro-thermal ablation techniques, as described in U.S. patent application Ser. No. 10/641,507, filed Aug. 15, 2003, published as U.S. Patent Publication No. 2004/0121486, which is incorporated herein by reference. In electrothermal ablation, the device has a reservoir cap that (1) is positioned over a reservoir opening to block the opening until release or exposure of the reservoir contents is desired and that (2) functions as a heat generator. Electric current is used to provide local heating of the reservoir cap in an amount effective to rupture the reservoir cap, opening the reservoir. "Electrothermal ablation" refers to the rupture by an electrically-induced thermal shock that causes the reservoir cap structure to fracture, and/or to a loss of structural integrity of the reservoir cap due to a phase change, (e.g., melting or vaporization), either or both of which are caused by the generation of heat within the reservoir cap as a result of electric current flowing through the reservoir cap. While not being bound to any theory, the heating causes the reservoir cap to degrade by melting (or vaporizing), thermal shock, and/or a mismatch in the coefficient of thermal expansion, thereby displacing the reservoir cap from over the reservoir and/or creating an aperture through the reservoir cap. This activation mechanism does not depend on a separate resistive heater element, for example, attached to an outer surface of a reservoir. (This rupture process is analogous to the process by which a conventional simple electrical fuse heats and then disintegrates (e.g., burns up) upon passage of an excessive amount of electrical current through it.) As used herein, the term "local heating" in reference to the reservoir cap refers to a significant temperature rise, which is local to the reservoir cap (e.g., the midpoint of the reservoir cap could be the hottest point). This temperature rise results from two phenomena: the heat generation and the heat loss occurring in the device. The local heating and rupturing typically occurs very quickly, on the order of 10 to 50 μs, which allows little heat to pass into the surrounding environment or into the reservoir contents, thereby minimizing any temperature increase in the environment surrounding the reservoir or limiting any temperature increase to the region immediately surrounding the reservoir cap.

The Substrate and Reservoirs

The substrate is the structural body (e.g., part of a device) in which the reservoirs are formed, e.g., it contains the etched, machined, or molded reservoirs. A reservoir is a well, a container. MEMS methods, micromolding, and micromachining techniques known in the art can be used to fabricate the substrate/reservoirs from a variety of materials. See, for example, U.S. Pat. No. 6,123,861 and U.S. Patent Application Publication No. 2002/0107470. Examples of suitable substrate materials include metals, ceramics, semiconductors, and degradable and non-degradable polymers. The substrate, or portions thereof, may be coated, encapsulated, or otherwise contained in a biocompatible material. Examples of coating materials include poly(ethylene glycol), polytetrafluoroethylene-like materials, inert ceramics, titanium, diamond-like carbon, and the like. In one embodiment, the substrate is formed of silicon.

The substrate can be flexible or rigid. In one embodiment, the substrate serves as the support for a drug delivery microchip.

The substrate can have a variety of shapes, or shaped surfaces. It can, for example, have a release side (i.e., an area having reservoir caps) that is planar or curved. The substrate may, for example, be in a shape selected from disks, cylinders, or spheres. In one embodiment, the release side can be shaped to conform to a curved tissue surface or into a body lumen. In another embodiment, the back side (distal the release side) is shaped to conform to an attachment surface.

The substrate may consist of only one material, or may be a composite or multi-laminate material, that is, composed of several layers of the same or different substrate materials that are bonded together.

Preferably, the substrate is hermetic, that is impermeable (at least during the time of use of the reservoir device) to the molecules to be delivered and to surrounding gases or fluids (e.g., water, blood, electrolytes or other solutions).

In another embodiment, the substrate is made of a strong material that degrades or dissolves over a defined period of time into biocompatible components. Examples of biocompatible polymers include poly(lactic acid)s, poly(glycolic acid)s, and poly(lactic-co-glycolic acid)s, as well as degradable poly(anhydride-co-imides).

The substrate thickness can vary. For example, the thickness of a device may vary from approximately 10 μm to several millimeters (e.g., 500 μm). Total substrate thickness and reservoir volume can be increased by bonding or attaching wafers or layers of substrate materials together. The device thickness may affect the volume of each reservoir and/or may affect the maximum number of reservoirs that can be incorporated onto a substrate. The size and number of substrates and reservoirs can be selected to accommodate the quantity and volume of drug formulation needed for a particular application, although other constraints such as manufacturing limitations or total device size limitations (e.g., for implantation into a patient) also may come into play. For example, devices for in vivo applications desirably would be small enough to be implanted using minimally invasive procedures.

The substrate includes at least two and preferably tens or hundreds of reservoirs. For example, one reservoir could be provided for each daily dose of drug required, for example, over a 3-, 8-, or 12-month course of treatment. A 15 mm×15 mm substrate, for example could include 400 reservoirs. Larger substrates could have more reservoirs, and for any size substrate, the number of reservoirs may vary, depending for example of how close together and how large the reservoir opening.

In one embodiment, the reservoir has a volume equal to or less than 500 μL (e.g., less than 250 μL, less than 100 μL, less than 50 μL, less than 25 μL, less than 10 μL, etc.) and greater than about 1 nL (e.g., greater than 5 nL, greater than 10 nL, greater than about 25 nL, greater than about 50 nL, greater than about 1 μL, etc.).

Drug and Release System

The drug delivery device includes a single drug or a combination of two or more drugs for release. The drug can comprise small molecules, large (i.e., macro-) molecules, or a combination thereof, having a bioactive effect. In one embodiment, the large molecule drug is a protein or a peptide. In various embodiments, the drug can be selected from amino acids, nucleic acids, oligonucleotides, polysaccharides, and synthetic organic molecules. In one embodiment, the drug is selected from nucleosides, nucleotides, and analogs and conjugates thereof. Representative examples of drugs include analgesics, anesthetics, anti-angiogenic molecules, antibiotics, antibodies, antineoplastic agents, antioxidants, antiviral agents, chemotherapeutic agents, gene delivery vectors, immunomodulators, ion channel regulators, metabolites, steroids, cytokines (e.g., interferons, interleukins), hormones sugars, psychotropic agents, vaccines, vitamins.

Examples of particular cardiac drugs that may be useful in the present medical devices include antiarrhythmic agents, antianginal agents, drugs for the treatment of congestive heart failure, and antithrombotic and fibrinolytic agents. Representative examples of antiarrhythmic agents include sodium channel blockers (e.g., quinidine, porcainamide, disopyramide, lidocaine, tocainide, mexiletine, encainide, and flecainide), beta-adrenergic blockers (e.g., propranolol, Acebutolol, Esmolol, and sotalol), drugs that prolong repolarization (e.g., sotalol and amiodarone), calcium channel blockers (e.g., verapamil, diltiazem, and mebefradil), adenosine, and digoxin. Representative examples of antianginal agents include nitrovasodilators (e.g., nitroglycerin, isosorbide dinitrate, and amyl nitrate), as well as calcium channel blockers and beta-adrenergic blockers. Representative examples of drugs for the treatment of congestive heart failure include inotropic agents (e.g., cardiac glycosides such as digoxin, beta-adrenergic agonists such as dobutamine, and phosphodiesterase inhibitors such as amrinone), angiotensin antagonists (e.g., angiotensin converting enzyme inhibitors such as enalapril, and angiotensin II receptor antagonists such as losartan), and diuretics (e.g., thiazides, furosemide, aldosterone antagonists, and potassium sparing antagonists such as triamterene). Representative examples of antithrombotic and fibrinolytic agents include anticoagulants (e.g., heparin and warfarin), anticoagulant antagonists (e.g., protamine, Vitamin K1), antiplatelet agents (e.g., aspirin, dextrans), tissue plasminogen activator, urokinase, streptokinase, Eminase, aminocaproic acid, and tranexamic acid. The drug delivery module can contain and deliver a wide variety of other drugs as well, alone or in combination with the specific ones identified above.

In a particularly preferred embodiment for use in the management of congestive heart failure, the drug is a natriuretic peptide. As used herein, the term "natriuretic peptide" includes the family of natriuretic peptides known in the art (e.g., ANP, BNP, CNP, and DNP), natural or recombinant natriuretic peptides, and natriuretic peptide analogues, such as described in U.S. Pat. No. 6,525,022 and U.S. Pat. No. 6,028,055, both to Lowe, et al., which are incorporated herein by reference.

The drug can be provided as part of a "release system," as taught in U.S. Pat. No. 5,797,898, the degradation, dissolution, or diffusion properties of which can provide a method for controlling the release rate of the molecules. The release system may include one or more pharmaceutical excipients. Suitable pharmaceutically acceptable excipients include most carriers approved for parenteral administration, including various aqueous solutions. Other excipients may be used to maintain the drug in suspensions as an aid to reservoir filling, stability, or release. Depending on the properties of the drug, such excipients may be aqueous or non-aqueous, hydrophobic or hydrophilic, polar or non-polar, protic or aprotic. See. e.g., U.S. Pat. No. 6,264,990 to Knepp et al. The release system optionally includes stabilizers, antioxidants, antimicrobials, preservatives, buffering agents, surfactants, and other additives useful for storing and releasing molecules from the reservoirs in vivo.

Reservoir Caps

As used herein, the term "reservoir cap" includes a membrane or other structure suitable for separating the contents of a reservoir from the environment outside of the reservoir. It generally is self-supporting across the reservoir opening, although caps having additional structures to provide mechanical support to the cap can be fabricated. Selectively removing the reservoir cap or making it permeable will then "expose" the contents of the reservoir to the environment (or selected components thereof) surrounding the reservoir. In preferred embodiments, the reservoir cap is selectively disintegrated. As used herein, the term "disintegrate" is used broadly to include without limitation degrading, dissolving, rupturing, fracturing or some other form of mechanical failure, as well as a loss of structural integrity due to a chemical reaction (e.g., electrochemical degradation) or phase change (e.g., melting) in response to a change in temperature, unless a specific one of these mechanisms is indicated. In one specific embodiment, the "disintegration" is by an electrochemical activation technique, such as described in U.S. Pat. No. 5,797,898. In another specific embodiment, the "disintegration" is by an electro-thermal ablation technique, such as described in U.S. patent application Ser. No. 10/641,507, filed Aug. 15, 2003.

In active release devices, the reservoir cap generally includes any material that can be disintegrated or permeabilized in response to an applied stimulus, e.g., electric field or current, magnetic field, change in pH, or by thermal, chemical, electrochemical, or mechanical means.

In one embodiment, the reservoir cap is a thin metal film and is impermeable to the surrounding environment (e.g., body fluids). In one variation, a particular electric potential is applied to the metal reservoir cap, which is then oxidized and disintegrated by an electrochemical reaction, to release the drug from the reservoir. Examples of suitable reservoir cap materials include gold, silver, copper, and zinc. In another variation, the reservoir cap is heated (e.g., using a resistive heater) to cause the reservoir cap to melt and be displaced from the reservoir to open it. This latter variation could be used, for example, with reservoir caps formed of a metal or a non-metal material, e.g., a polymer. In yet another variation, the reservoir cap is formed of a polymer or other material that undergoes a temperature-dependent change in permeability such that upon heating to a pre-selected temperature, the reservoir is rendered permeable to the drug and bodily fluids to permit the drug to be released from the reservoir through the reservoir cap.

In still another embodiment, the reservoir cap is formed of a conductive material, such as a metal film, through which an electrical current can be passed to electrothermally ablate it, as described in U.S. patent application Ser. No. 10/641,507, filed Aug. 15, 2003. Representative examples of suitable reservoir cap materials include gold, copper, aluminum, silver, platinum, titanium, palladium, various alloys (e.g., Au/Si, Au/Ge, Pt—Ir, Ni—Ti, Pt—Si, SS 304, SS 316), and silicon doped with an impurity to increase electrical conductivity, as known in the art. In one embodiment, the reservoir cap is in the form of a thin metal film. In one embodiment, the reservoir cap is part of a multiple layer structure, for example, the reservoir cap can be made of multiple metal layers, such as a multi-layer/laminate structure of platinum/titanium/platinum. The reservoir cap is operably (i.e. electrically) connected to an electrical input lead and to an electrical output lead, to facilitate flow of an electrical current through the reservoir cap. When an effective amount of an electrical current is applied through the leads and reservoir cap, the temperature of the reservoir cap is locally increased due to resistive heating, and the heat generated within the reservoir cap increases the temperature sufficiently to cause the reservoir cap to be electrothermally ablated (i.e., ruptured).

In passive release devices, the reservoir cap is formed from a material or mixture of materials that degrade, dissolve, or disintegrate over time, or that do not degrade, dissolve, or disintegrate, but are permeable or become permeable to molecules or energy. Representative examples of reservoir cap materials include polymeric materials, and non-polymeric materials such as porous forms of metals, semiconductors, and ceramics. Passive semiconductor reservoir cap materials include nanoporous or microporous silicon membranes.

Characteristics can be different for each reservoir cap to provide different times of release of drug formulation. For example, any combination of polymer, degree of crosslinking, or polymer thickness can be modified to obtain a specific release time or rate.

Any combination of passive and/or active release reservoir cap can be present in a single drug delivery module. For example, the reservoir cap can be removed by electrothermal ablation to expose a passive release system that only begins its passive release after the reservoir cap has been actively removed. Alternatively, a given device can include both passive and active release reservoirs.

Means for Controlling Drug Release

The drug delivery device includes a control means to control the time at which the drug is released from the device, and into the patient's body.

In one embodiment, the means for controllably releasing the drug provides selective actuation of each reservoir, which is done under the control of a microprocessor. Preferably, such means includes an input source, a microprocessor, a timer, a demultiplexer (or multiplexer), and a power source. As used herein, the term "demultiplexer" also refers to multiplexers. The power source provides energy to activate the selected reservoir, i.e., trigger release of drug from the particular reservoir desired for a given dose. The microprocessor can be programmed to initiate the disintegration or permeabilization of the reservoir cap in response at a pre-selected time or in response to one or more of signals or measured parameters, including receipt of a signal from another device (for example by remote control or wireless methods) or detection of a particular condition using a sensor such as a biosensor.

The microchip device can also be activated or powered using wireless means, for example, as described in U.S. Pat. No. 2,002,0072784 A1 to Sheppard et al. The telemetry means shown in FIG. 4 can be employed in this manner, as well as to communicate instructions for or power the electrical stimulation.

In one embodiment, the medical device includes a substrate having a two-dimensional array of reservoirs arranged therein, a release system comprising drug contained in the reservoirs, anode reservoir caps covering each of the reservoirs, cathodes positioned on the substrate near the anodes, and means for actively controlling disintegration of the reservoir caps. The energy drives a reaction between selected anodes and cathodes. Upon application of a small potential between the electrodes, electrons pass from the anode to the cathode through the external circuit causing the anode material (reservoir cap) to oxidize and dissolve into the surrounding fluids, exposing the release system containing the drug for delivery to the surrounding fluids, e.g., in vivo. The microprocessor directs power to specific electrode pairs through a demultiplexer as directed by a PROM, remote control, or biosensor.

In another embodiment, the activation energy initiates a thermally driven rupturing or permeabilization process, for example, as described in PCT WO 01/12157. For example, the means for controlling release can actively disintegrate or permeabilize a reservoir cap using a resistive heater. The resistive heater can cause the reservoir cap to undergo a phase change or fracture, for example, as a result of thermal expansion of the reservoir cap or release system, thereby rupturing the reservoir cap and releasing the drug from the selected reservoir. The application of electric current to the resistive heater can be delivered and controlled using components as described above for use in the electrochemical disintegration embodiment. For example, a microprocessor can direct current to select reservoirs at desired intervals.

In yet another embodiment, control means controls electro-thermal ablation of the reservoir cap. For example, the drug delivery device could include a reservoir cap formed of an electrically conductive material, which prevents the reservoir contents from passing out from the device; an electrical input lead connected to the reservoir cap; an electrical output lead connected to the reservoir cap; and a control means to deliver an effective amount of electrical current through the reservoir cap, via the input lead and output lead, to heat and rupture the reservoir cap to release the drug. In one embodiment, the reservoir cap and conductive leads are formed of the same material, where the temperature of the reservoir cap increases locally under applied current because the reservoir cap is suspended in a medium that is less thermally conductive than the substrate. Alternatively, the reservoir cap and conductive leads are formed of the same material, and the reservoir cap has a smaller cross-sectional area in the direction of electric current flow, where the increase in current density through the reservoir cap causes an increase in localized heating. The reservoir cap alternatively can be formed of a material that is different from the material forming the leads, wherein the material forming the reservoir cap has a different electrical resistivity, thermal diffusivity, thermal conductivity, and/or a lower melting temperature than the material forming the leads. Various combinations of these embodiments can be employed as described in U.S. patent application Ser. No. 10/641,507, filed Aug. 15, 2003.

In one embodiment, the drug delivery device utilizes an accelerated release mechanism. In one embodiment, a positive displacement feature can be included to facilitate release of the drug from the reservoirs. For example, the device may include an osmotic engine or water-swellable component, which can be used to drive a drug formulation from the reservoirs. For example, such a feature can provide very fast release of drug the efficacy of which is dependent on a fast pharmacokinetic pulsatile profile. As used herein, the term "accelerated release" refers to an increase in the transport rate of drug out of the reservoir relative to the transport rate of the drug solely by diffusion down its own chemical gradient. The terms also refer to expelling reservoir contents that would not otherwise egress from an open reservoir, i.e., where no or negligible diffusion could occur.

B. The Cardioversion Means

The cardioversion means preferably comprises one or more device components known in the art, for cardiac pacing, cardioverting, and/or defibrillating. In one embodiment, the cardioversion means comprises a signal generator connected to at least two electrodes suitable for operable engagement with a cardiac muscle of a patient. The signal generator is generated between the two electrodes suitable for operable engagement with a cardiac muscle of a patient. The electrodes are connected to a power source, such as a high energy capacitor and lithium battery, which provide the energy and power source respectively for cardiac stimulation.

C. The Pacing Means

The pacing means preferably comprises one or more device components known in the art, for cardiac pacing. In one embodiment, the pacing means comprises a signal generator connected to at least two electrodes suitable for operable engagement with a cardiac muscle of a patient as a single chamber pacemaker. The electrodes are connected to a pulse generator, power source, such as an energy storage capacitor and lithium battery, which provide the energy and power source respectively for cardiac stimulation and sensing of cardiac activity. In another embodiment, the pacing means comprises a signal generator connected to at least four electrodes suitable for operable engagement with a cardiac muscle of a patient as a dual chamber pacemaker.

D. The Monitoring Means

The monitoring means preferably comprises one or more device components known in the art for physiological monitoring (electrogram (ECG or EEG), $O_2$ saturation, pressure, temperature, pH, or loads on tissue structure at various in vivo locations). In one embodiment, the monitoring means comprises a physiologic signal sensing and discrimination in the determination of a changing physiological condition which may induce the initial delivery or changing the delivery prescription of drug therapy.

As used herein, the term "operable engagement" in reference to the electrodes or sensors and cardiac tissues refers to sufficient proximity to the cardiac tissue for the electrode or sensor to operate effectively as known in the art; the electrodes or sensors may or may not be in direct contact with the cardiac tissue.

E. Microcontroller Means and Other Components

The microcontroller means controls the signal generator and/or receives the monitored electrogram or ECG signals and controls the control means of the drug device module. As used herein, the term "microcontroller" is used to refer to microprocessors, state machines, digital logic, or a combination thereof, which is operable to control (i) the drug delivery module; (ii) the cardiac electrode module for stimulation, monitoring, or both; (iii) the interaction of the drug delivery module and the cardiac electrode module; or (iv) a combination thereof.

In one embodiment, the control circuitry includes a microprocessor, a timer, a demultiplexer, and an input source (for example, a memory source, a signal receiver, or a biosensor), a telemetry communication circuit, and a power source. The timer and demultiplexer circuitry can be designed and incorporated directly onto the surface of the microchip during electrode fabrication, or may be incorporated in a separate integrated circuit. The criteria for selection of a microprocessor are small size, low power requirement, and the ability to translate the output from memory sources, communications signals, signal receivers, or biosensors into an address for the direction of power through the demultiplexer to a specific reservoir on the microchip device (see, e.g., Ji, et al., *IEEE J Solid-State Circuits* 27:433-43 (1992)). Selection of a source of input to the microprocessor such as memory sources, signal receivers, or biosensors depends on the microchip device's particular application and whether device operation is preprogrammed, controlled by remote means, or controlled by feedback from its environment (i.e., biofeedback).

A microprocessor is used in conjunction with a source of memory (such as an erasable programmable read only memory (EPROM), an on-board flash memory, and/or an external EEPROM), a timer, a demultiplexer, and a power source such as a battery (e.g., a lithium battery). A programmed sequence of events including the time a reservoir is to be opened and the location or address of the reservoir can be stored into the memory source by the user. When the time for exposure or release has been reached as indicated by the timer, the microprocessor sends a signal corresponding to the address (location) of a particular reservoir to the demultiplexer. The demultiplexer routes an input, such as an electric potential or current, to the reservoir addressed by the microprocessor.

Typically, the operation of the drug delivery module will be controlled by an on-board (i.e., within the package) microprocessor. The output signal from the device, after conditioning by suitable circuitry if needed, will be acquired by the microprocessor. After analysis and processing, the output signal can be stored in a writeable computer memory chip, and/or can be sent (e.g., wirelessly) to a remote location away from the microchip. Power can be supplied to the medical device locally by a battery or remotely by wireless transmission.

Sensors

In an optional embodiment, the microchip device includes a sensor or sensing component. For example, the sensor or sensing component can be located in a reservoir or can be attached to the device substrate or encasement. The sensor can operably communicate with the drug delivery module, the cardiac stimulator, or both, e.g., through a microprocessor, to control or modify the drug release variables, including dosage amount and frequency, time of release, effective rate of release, selection of drug or drug combination, as well as the time, duration, and frequency of electrical stimulation delivered to cardiac tissue, and the like. The "sensing component" includes a component utilized in measuring or analyzing the presence, absence, or change in a chemical or ionic species, energy, or one or more physical properties (e.g., pH, pressure). Types of sensors include biosensors, chemical sensors, physical sensors, or optical sensors. Further examples of such sensors and sensor components are described in PCT WO 01/64344. The sensor or sensing component detects (or not) the species or property at the site of in vivo implantation (e.g., in a bodily fluid or tissue), and further may relay a signal to the microprocessor used for controlling release from the microchip device, as detailed below. Such a signal could provide feedback on and/or finely control the release of drug and electrical stimulation.

There are several different options for receiving and analyzing data obtained with devices located in the microchip devices. Active microchip devices may be controlled by local microprocessors or remote control. Biosensor information may provide input to the controller to determine the time and type of activation automatically, with human intervention, or a combination thereof. In one embodiment, the medical device includes a biosensor that can detect an oncoming of a biological event, and the device can initiate or alter the drug therapy or stimulation therapy or both provided by the medical device such that the effects of the biological event are limited or prevented. The timing of drug administration or a change in drug dosing can be done with or without the patient's knowledge.

In one embodiment, operation of the drug delivery module is controlled by an on-board (i.e., within the package) microprocessor. After analysis and processing, the output signal can be stored in a writeable computer memory chip, and/or can be sent (e.g., wirelessly) to a remote location away from the microchip. Power can be supplied to the medical device locally by a battery or remotely by wireless transmission.

In one embodiment, the medical device includes one or more biosensors (which may be sealed in reservoirs until needed for use) that are capable of detecting and/or measuring signals within the body of a patient. As used herein, the term "biosensor" includes sensing devices that transduce the chemical potential of an analyte of interest into an electrical signal (e.g., an ion selective field effect transistor or ISFET), as well as electrodes that measure electrical signals directly or indirectly (e.g., by converting a mechanical or thermal energy into an electrical signal). For example, the biosensor may measure intrinsic electrical signals (ECG, internal electrogram, or other cardiac signals), $O_2$ saturation, pressure, temperature, pH, or loads on tissue structures at various in vivo locations. The electrical signal from the biosensor can then be measured, for example by a microprocessor/controller, which then can transmit the information to a remote controller, another local controller, or both. For example, the system can be used to relay or record information on the patient's vital signs or the implant environment, such as drug concentration.

Packaging

The medical devices described herein will typically be packaged into to hermetically sealed package, e.g., in a titanium encasement, which essentially exposes only the reservoir caps, stimulation electrodes, and sensing electrodes when included. These microelectronic device packages are typically made of an insulating or dielectric material such as aluminum oxide or silicon nitride. Low cost packages can also be made of ceramics, plastics, or reinforced epoxies. The package serves to allow all components of the device to be placed in close proximity and to facilitate the interconnection of components to power sources and to each other, while protecting the electronics from the environment. The packaging can be coated with a biocompatible material, such as poly(ethylene glycol), polytetrafluoroethylene-like materials, inert ceramics, titanium, diamond-like carbon, and the like.

In one embodiment, the device comprises an outer layer comprising a single layer or a multi-layer/laminate structure that includes combinations of silicon oxide ($SiO_x$), silicon nitride ($SiN_x$) or silicon carbide ($SiC_x$). In one embodiment, photoresist is patterned on top of the dielectric to protect it from etching except on the reservoir caps covering each reservoir. The dielectric material can be etched by physical or chemical etching techniques. The purpose of this film is to protect the reservoir caps and leads from corrosion, degradation, delamination, or dissolution in all areas where they do not have to be exposed to the surrounding environment, to shield electrically active components from the in vivo environment, and to enhance the biostability of the device materials.

Methods of Making the Devices

The devices and modules described herein can be made using techniques known in the art and/or described herein. Certain methods are described in U.S. Pat. No. 5,797,898; U.S. Pat. No. 6,123,861; U.S. Patent Application Publication No. 2002/0107470; and U.S. Patent Application Publication No. 2002/0151776, which are hereby incorporated by reference in their entirety. One skilled in the art can fabricate, or obtain the components and assemble them into, the medical devices described herein. The assembly of a complete medical device may involve a number of packaging steps which can include (1) attachment of electrical leads to the microchip, (2) filling of the reservoirs with a release system comprising drug, (3) sealing the reservoirs, (4) integration with electronic components and power sources and electrodes, and (5) placing the microchip(s) and associated components within a single enclosure or "package."

Operation and Use of the Devices

Operation of the implantable device in arrhythmia therapy and in cardiac monitoring is described above. In one, the drug delivery module is controlled by a pre-programmed microprocessor to open one or a portion of the reservoirs intermittently (that is, a different one or more reservoirs after predetermined time intervals) to effect release intermittently, e.g., in a pulsatile manner. In other variations, the microprocessor (and thus release) is controlled by a sensor, e.g., a biosensor, or by remote control. The microprocessor also coordinates and controls delivery of the electrical signals to the electrodes connected to the cardiac tissue to be stimulated.

Methods of using microchip devices for controlled release of drug are further described in U.S. Pat. No. 5,797,898 and No. 6,123,861; and PCT WO 02/30401, WO 02/30264, WO 01/91902, WO 01/64344, WO 01/41736, WO 01/35928, and WO 01/12157.

In one embodiment, the drug delivery module is for subcutaneous drug delivery, to release drugs into the subcutaneous region which then diffuse into regional tissue or into body fluid-containing structures, including, for example, the cardiovascular system, the lymphatic system, the respiratory system, the digestive system, the central nervous system (cerebral spinal fluid), or the genitourinary system. With the device, a drug can be administered to treat one or more of these tissues or structures or fluids within the structures, or can be transported through these tissues or structures to distal treatment locations or to cellular binding sites.

In another embodiment, the drug delivery module provides direct communication between the source of the drug (e.g., a reservoir) and the particular fluid-containing structure of interest, so that when drug is released, it enters the fluid without contacting the subcutaneous region. This could be useful, for example, for administrating a drug that if released in the subcutaneous space would cause inflammation, irritation, other tissue injury/dysfunction, or would diffuse too slowly into a fluid-containing structure to achieve an effective concentration in the fluid (e.g., because of clearance mechanisms). For example, the device could directly release a therapeutic agent into one or more body cavities or tissue lumens, including an intrathecal space, an intracranial space, an abdominal/peritoneal space, a thoracic space, an intrapericardial space, a renal space, or a hepatic space. For example, the substrate could have a shape that is compatible with the fluid-containing structure, such as tubular to reside within a blood vessel (e.g., intravascular), rounded and buoyant to float in the bladder, or curved to conform to the eye. The control circuitry and power needed to activate the reservoir caps can be located in a control module outside or inside of the fluid-containing structure. If the control module is located external to the fluid-containing structure, electrical conductors can be used to connect to the reservoir caps.

In one embodiment, a drug delivery module includes a catheter which can be inserted into the tissue lumen or structure of interest and which has one or more drug-containing reservoirs fabricated therein, for example at a distal portion of the catheter. The body of the catheter serves as the substrate in which tens or hundreds of micro-reservoirs are arrayed around the catheter body at the distal tip portion. Advantageously, the power source and control hardware can be located at a proximal end of the catheter, so they need not fit into or be located at the delivery site. The electrical traces could be built into the catheter body or supported on an inner or outer surface of the catheter body. See U.S. Patent Application No. 2002/0111601, which disclosed one embodiment of a catheter type implantable medical device, but which utilizes a different reservoir opening technology than the electrothermal ablation system described herein. Optionally, the catheter can have an internal fluid passageway extending between a proximal end portion and a distal end portion. The fluid passageway can be in communication with an infusion pump and a reservoir (e.g., a refillable reservoir containing a therapeutic fluid), so that the device can deliver a therapeutic fluid through the passageway to the delivery site. In one embodiment, the pump is placed abdominally in a subcutaneous pocket, and the catheter is inserted into the intrathecal space of the spine, tunneled under the skin and connected to the pump. Such an embodiment could be used, for example, in the management of chronic pain or for spasticity therapy. The microarray of drug-containing reservoirs can be provided (i) on or in the body of the catheter, (ii) in a substrate device that is located at the proximal end of the catheter and releases drug into an infusion fluid pumped across the microarray openings to form a fluid/drug mixture that is pumped through the fluid passageway of the catheter, or (iii) in a combination of these. In one embodiment, the distal tip portion of the catheter includes one or more biological sensors to detect patient conditions that indicate the desirability or need for drug release. The sensors could extend from or be on the surface of the tip portion of the catheter body or could be located within one or more reservoirs. In one version, the device could include one catheter having a sensor on the distal end portion for implantation at a first site in vivo, and a second catheter having drug-containing reservoirs on the distal end portion for implantation at a second site in vivo.

Treatment and Management of Congestive Heart Failure

In various embodiments, an implantable drug delivery device is provided to deliver a natriuretic peptide alone or in combination with other drugs for use in the treatment or management of congestive heart failure (CHF). The other drugs may be those useful in treatment or management of hypertension or arrhythmia, as a patient suffering from CHF may also suffer from these conditions. Examples of additional drugs for release from the implantable drug delivery device include diuretics, vasodilators, and inotropic agents, such as anti-arrhythmic agents, $Ca^+$ channel blocking agents, anti-adrenergics/sympatholytics, and renin angiotensin system antagonists. A significant improvement in the care of CHF patients can be realized by a device that can both monitor relevant parameters and deliver appropriate amounts of natriuretic peptide and/or other drugs in response to the status of the patient as indicated by the relevant parameters.

In one embodiment, drug release from the device is controlled by an implanted controller that monitors hemodynamic parameters, ECG parameters, or both, to determine when the natriuretic peptide should be delivered. For example, the implanted medical device could include an implanted drug delivery module and an implanted monitoring module, wherein interaction of the two modules is controlled by a microcontroller. In this way, the modules cooperate to deliver the appropriate amounts and types of drugs in response to the real time needs of the patient, without the need for human activity between the monitoring and the drug delivery steps. Alternatively, the implanted monitoring module can send information about the patient to the patient or doctor, so that the patient or doctor can activate (or reprogram) the implanted drug delivery module.

In one embodiment, drug release from the implantable drug delivery device is controlled externally, for example under the control of the patient or a physician. For example, if the patient has been previously treated with natriuretic peptide and his or her dose-response is already known, then the patient or physician can then use telemetry to activate the release of an appropriate amount of drug over the appropriate duration, based any of a variety of measured patient parameters. For example, the patient could monitor his or her short term weight gain (indicative of fluid retention) or a non-invasive pressure measurement (e.g., using an arm cuff) could be taken. In yet another example, telemetered pressure information from an implanted monitor could be used all be used to determine the need for and amount of natriuretic peptide or other drug to be released. Implantable devices for detecting and diagnosing conditions associates with congestive heat failure are known and described for example in U.S. Pat. No. 6,328,699 to Eigler, et al., which is incorporated herein by reference. In one embodiment, the implanted monitor may include a low power transmitter configured to transmit information transcutaneously to a remote receiver, which could include a display screen or other means for communicating instructions to the patient, or it could communicate instructions to a separately implanted drug delivery module. Such a system may also include an apparatus (e.g., a handheld device) for wirelessly or hardwired communication of information to a base location. This could be used, for example, to transmit information concerning the patient's condition back to a hospital or doctor's office, or to transmit information concerning the patient's prescription usage back to a pharmacy.

In one embodiment, the drug delivery device releases a natriuretic peptide (alone or in combination with diuretics, vasodilators, and/or inotropic agents as a bolus, continuously, or in a pulsatile manner to prevent fluid overload, vasoconstriction, and reduced myocardial contractility) in the treatment or management of CHF. In a related embodiment, the device could include a drug useful in the treatment or management of hypertension or arrhythmia, such as anti-arrhythmic agents, $Ca^+$ channel blocking agents, anti-adrenergics/sympatholytics, and renin angiotensin system antagonists. In these embodiments, the drug delivery device optionally may be operatively linked to a monitoring or sensing device, so that the dosing is tailored to the patient's real time needs. Alternatively, the device is preset or preprogrammed to deliver a particular dosage and may not require the monitoring capability. In one variation of this embodiment, the device, after implantation, can be reprogrammed (e.g., wirelessly) periodically, as needed. With daily dosing of a natriuretic peptide, for example, it is believed that a patient could avoid or defer the onset of an acute CHF exacerbation. It is also possible that low doses of natriuretic peptide, insufficient to palliate the symptoms of an acute CHF condition or insufficient to maintain hemodynamic stability, will be effective in reducing the rate or extent of cardiac remodeling.

The implantable drug delivery module can be any device that is capable of storing and controllably releasing the natriuretic peptide or other drug useful in the treatment or management of CHF. Preferably, it is capable of releasing doses of drug on a frequent basis for a period greater than six months, e.g., up twelve months or more. Examples of suitable devices include those described in U.S. Pat. No. 5,797,898; U.S. Pat. No. 6,123,861; and U.S. Pat. No. 6,491,666, and U.S. patent application Ser. No. 10/641,507, filed Aug. 15, 2003, which are incorporated herein by reference.

In one embodiment, the device includes a means for monitoring patient parameters, a means for storing the monitored parameter values, and a means for processing the monitored values. The means for monitoring patient parameters, the means for storing the monitored parameter values, and the means for processing the monitored values are, or can be readily adapted from, those known in the art. In various embodiments, the means for processing parameters, e.g., the processing unit, may be any processor, microprocessor, CPU, logic circuit or other device that responds to and processes computer-executable instructions. The means for storing can be, for example, read only memory (ROM, PROM, EPROM, EEPROM, etc.), random access memory (RAM), and other storage devices, such as hard disks, floppy disks, optical disks, tapes and other types of computer-readable media. In one embodiment, a physician or patient programs the processing means to determine the timing and dosage of release of the one or more drugs in response to the monitored values (or a change therein).

Devices and methods for monitoring patient parameters are well known. These means may be used externally or internally with respect to the patient. Examples of useful patient parameters to monitor include blood pressures, cardiac electrical signals, tissue electrical impedance, blood oxygen, blood oxygen saturation, natriuretic peptide levels, and combinations thereof. Implantable electronic systems known for use in cardiovascular application, which can be used in the devices and methods described herein include those for monitoring the heart's electrical activity (real time and processed electrograms can be used to control the timing and amount of electrical energy delivered to various cardiac sites to restore and maintain normal cardiac rhythm, defibrillate arrhythmic tissue, and regulate blood flow provided by assist devices implanted or external to the patient), cardiovascular pressures (which is useful to understand the hemodynamic status of the patient, including venous pressure, which is an indicator of pulmonary congestion, and arterial pressure, which is an indicator of vasoconstriction and the pumping capacity of the heart), blood oxygen and blood oxygen saturation (for example, oxygen saturation of venous and arterial blood provides information about the oxygen demand of the body and the gas exchange performance of the lungs, which is directly related to the level of congestion of the lungs and the efficiency of blood flow through the lungs), and electrical impedance of the lungs and thorax (for example, impedance changes with the fluid content of tissue and is used to indicate the extent of congestion of the lungs and heart tissue).

In one embodiment, the means for controlling drug release is integrated into or combined with the drug delivery module, wherein drug release is based upon the monitored parameters of a patient. One or more of these means can be internal to the patient, i.e., implanted. Two or more of the means can be operably linked with one another by wires or by telemetry. See, e.g., PCT WO 01/64344 and U.S. Patent Application No. 2002/0072784 A1.

Publications cited herein and the materials for which they are cited are specifically incorporated by reference. Modifications and variations of the methods and devices described herein will be obvious to those skilled in the art from the foregoing detailed description. Such modifications and variations are intended to come within the scope of the appended claims.

We claim:

1. A medical device for controlled drug delivery in cardiac care in a patient comprising:
    an implantable drug delivery module which comprises
        a plurality of reservoirs,
        a release system contained in each of the reservoirs, wherein the release system comprises at least one drug,
        a plurality of discrete electrically conductive reservoir caps separating the release system from an environment outside of the reservoirs, and
        a means for disintegrating one or more of the reservoir caps by electrothermal ablation to release the drug from one or more of the reservoirs;
    one or more electrodes or sensors for operable engagement with a cardiac tissue of a patient, wherein the one or more electrodes or sensors are useful for cardiac monitoring, cardiac stimulation, or both; and
    at least one microcontroller for controlling operational interaction of the drug delivery module and the cardiac electrode or sensor,
    wherein the means for disintegrating by electrothermal ablation comprises (i) an electrical input lead and an electrical output lead which are in direct physical and electrical connection to at least one of said reservoir caps, (ii) a power source, and (iii) a control means for controlling application of an electric current from the power source through said at least one of the reservoir caps, via the input and output leads.

2. The device of claim 1, wherein the one or more electrodes or sensors comprise ECG monitoring electrodes.

3. The device of claim 1, wherein the one or more electrodes or sensors comprise cardioversion electrodes.

4. The device of claim 1, wherein the one or more electrodes or sensors comprise cardiac pacing electrodes.

5. The device of claim 1, wherein the microcontroller is adapted to initiate release of the drug from the drug delivery module immediately upon receiving a signal from the one or more electrodes, which signal is indicative of onset of an arrhythmia.

6. The device of claim 5, wherein the device is adapted to detect non-sustained ventricular tachycardias, changes in heart rate variability, or both.

7. The device of claim 1, further comprising a defibrillator for delivering a cardioversion shock.

8. The device of claim 7, wherein the drug comprises an anti-coagulant, an analgesic, or both.

9. The device of claim 8, wherein the microcontroller, upon receiving a signal from the one or more electrodes or sensors indicative of an atrial fibrillation, is adapted to release the drug and then after a predetermined delay to initiate the cardioversion shock, wherein the delay is of a duration effective to permit the drug to take effect.

10. The device of claim 9, the device is adapted to reconfirm the arrhythmia following the predetermined delay and, if detected, to deliver the cardioversion shock.

11. The device of claim 1, which is adapted to treat ventricular arrhythmias.

12. The device of claim 1, further comprising a pacemaker having electrodes for contacting the cardiac muscle for monitoring of a patient and transmission of pacing signals.

13. The device of claim 12, wherein the drug comprises an anti-arrhythmic drug, which, upon release, is effective to reduce the frequency of induced pacing activity.

14. The device of claim 12, wherein the drug is one which, upon release, is effective to increase the sensitivity of myocardial tissue to the pacemaker stimulation pulse to effectively reduce pacing thresholds.

15. The device of claim 1, comprising a cardioversion means which comprises a signal generator connected to at least two of the one or more electrodes, wherein the microcontroller controls the signal generator and the means for disintegrating one or more of the reservoir caps.

16. The device of claim 15, wherein the cardioversion means is implantable.

17. The device of claim 1, comprising an ECG monitor for monitoring for a change in heart rate variability.

18. The device of claim 17, wherein the drug is one which, upon release, is used to reduce heart transplant rejection and the monitor is adapted to measure heart rate variability on a daily basis.

19. The device of claim 17, wherein the drug is one which, upon release, is effective to prevent angina or myocardial infarction or both.

20. The device of claim 17, wherein the microcontroller is adapted to release the drug as a function of the changes in the ST segment measured by the ECG monitor.

21. The device of claim 1, further comprising a cardiac monitoring means for measuring electrogram signals from the heart, wherein the microcontroller is adapted to receive a signal from the cardiac monitoring means and to control the means for disintegrating one or more of the reservoir caps.

22. The device of claim 21, wherein the cardiac monitoring means is implantable.

23. The device of claim 1, wherein the one or more electrodes or sensors are on an outer surface of a hermetically sealed encasement containing the drug delivery module and the microcontroller.

24. The device of claim 1, further comprising a hermetically sealed encasement containing the drug delivery module and microcontroller, wherein the one or more electrodes or sensors extend a distance from the hermetically sealed encasement.

25. The device of claim 24, further comprising a flexible catheter connecting the one or more electrodes to the encasement.

26. The device of claim 1, further comprising telemetry components in operable communication with the microcontroller.

27. The device of claim 1, wherein the drug delivery module comprises a microchip drug delivery device.

28. The device of claim 1, further comprising one or more physiological sensors operable to deliver a signal to the microcontroller.

29. The device of claim 1, wherein the one or more electrodes or sensors monitor one or more patient parameters useful in treatment or management of congestive heart failure.

30. The device of claim 1, wherein the drug comprises a natriuretic peptide.

31. The device of claim 1, wherein the drug comprises an antiarrhythmic agent, an antianginal agent, an antithrombotic agent, or an fibrinolytic agent.

32. A medical device for drug delivery to a cardiac care patient comprising:
an implantable drug delivery module which comprises
a plurality of reservoirs,
a release system contained in each of the reservoirs, wherein the release system comprises at least one drug,
a plurality of discrete metal reservoir caps separating the release system from an environment outside of the reservoirs,
an electrical input lead and an electrical output lead which are in direct physical and electrical connection to each of the reservoir caps,
a power source, and
a microcontroller for controlling application of an electric current from the power source through said at least one of the reservoir caps, via the input and output leads, in an amount effective to disintegrate the reservoir cap by electrothermal ablation to release the at least one drug from one or more of the reservoirs; and
one or more electrodes or sensors for operable engagement with a cardiac tissue of a patient, wherein the one or more electrodes or sensors are useful for cardiac monitoring, cardiac stimulation, or both.

33. An implantable medical device comprising:
a body;
at least one reservoir in the body;
reservoir contents contained in the at least one reservoir, wherein the reservoir contents comprises a sensor for measuring or analyzing the presence, absence, or change in a chemical or ionic species indicative of cardiac health;
an electrically conductive reservoir cap covering the at least one reservoir to separate the reservoir contents from an environment outside of the reservoir;
conducting leads to and from the reservoir cap; and
a power source and a controller for selectively delivering an electric current through the reservoir cap effective to disintegrate the reservoir cap by electrothermal ablation to release or expose the reservoir contents;
wherein the reservoir cap and the conducting leads to and from the reservoir cap are configured to provide, upon the application of electrical current to the conducting leads, an increase in electrical current density in the reservoir cap relative to the current density in the conducting leads to and from the reservoir cap.

34. The device of claim 33, further comprising one or more electrodes for operable engagement with a cardiac tissue of a patient, wherein the one or more electrodes are useful for cardiac monitoring, cardiac stimulation, or both.

35. The device of claim 33, which comprises a plurality of discrete reservoirs, each of which are covered by an electrically conductive reservoir cap connected to a pair of conducting leads.

36. The device of claim 33, further comprising one or more active agent reservoirs that contain an antiarrhythmic agent, an antianginal agent, a natriuretic peptide, an antithrombotic agent, or an fibrinolytic agent, for controlled release.

37. The device of claim 34, further comprising at least one microcontroller for controlling operational interaction of the drug delivery module and the one or more electrodes or sensors.

38. The device of claim 33, wherein the material forming the reservoir cap has a different electrical resistivity, thermal diffusivity, and/or thermal conductivity, than the material forming the conducting leads to and from the reservoir cap.

39. The device of claim 33, wherein the material forming the reservoir cap has a lower melting temperature than the material forming the conducting leads to and from the reservoir cap.

* * * * *